(12) United States Patent
Ward et al.

(10) Patent No.: US 10,300,286 B2
(45) Date of Patent: May 28, 2019

(54) TOOLS AND ASSEMBLIES THEREOF FOR IMPLANTABLE MEDICAL DEVICES

(71) Applicant: Medtronic, Inc., Minneapolis, MN (US)

(72) Inventors: Sean Ward, Dublin (IE); Rónán Wood, Co. na Gaillmhe (IE); Gwenda McMullin, Galway (IE); Paula McDonnell, Galway (IE); Aram Jamous, Co Galway (IE)

(73) Assignee: Medtronic, Inc., Minneapolis, MN (US)

( * ) Notice: Subject to any disclaimer, the term of this patent is extended or adjusted under 35 U.S.C. 154(b) by 1249 days.

(21) Appl. No.: 14/040,110

(22) Filed: Sep. 27, 2013

(65) Prior Publication Data

US 2015/0094735 A1 Apr. 2, 2015

(51) Int. Cl.
*A61N 1/362* (2006.01)
*A61N 1/372* (2006.01)
(Continued)

(52) U.S. Cl.
CPC .......... *A61N 1/362* (2013.01); *A61M 25/0141* (2013.01); *A61N 1/056* (2013.01); *A61N 1/3756* (2013.01); *A61N 1/37205* (2013.01)

(58) Field of Classification Search
CPC .......... A61M 25/0141; A61M 25/0138; A61M 25/0144; A61B 2017/00331; A61B 2017/003
(Continued)

(56) References Cited

U.S. PATENT DOCUMENTS

| 3,814,104 A | 6/1974 | Irnich et al. |
| 4,103,690 A | 8/1978 | Harris |

(Continued)

FOREIGN PATENT DOCUMENTS

| EP | 1365702 | 8/2008 |
| EP | 1670360 | 9/2010 |

(Continued)

OTHER PUBLICATIONS

Marshall et al., "Substernal Lead/Electrode Concepts", U.S. Appl. No. 62/089,417, filed Dec. 9, 2014, 28 pages.
(Continued)

*Primary Examiner* — Diane D Yabut
*Assistant Examiner* — Majid Jamialahmadi

(57) ABSTRACT

A tool has an outer assembly, which includes a deployment tube, extending around, and moveable with respect to an inner assembly of the tool; the inner assembly includes a single pull wire and a distal member configured to engage an end of an implantable medical device. The deployment tube includes an articulating segment located just proximal to an enlarged distal-most portion, which contains the device and the distal member. Relatively soft and stiff sections of a composite sidewall define the articulating segment and extend alongside one another, such that, when the pull wire is actuated, the composite sidewall causes bending of the segment in two directions. A handle assembly of the tool includes a control member for the pull wire, and may further include a flushing subassembly that has a connector port located at an end of the handle assembly that is opposite a proximal port of the handle.

15 Claims, 9 Drawing Sheets

(51) Int. Cl.
*A61N 1/375* (2006.01)
*A61N 1/05* (2006.01)
*A61M 25/01* (2006.01)

(58) Field of Classification Search
USPC .......................................................... 606/129
See application file for complete search history.

(56) References Cited

U.S. PATENT DOCUMENTS

| | | | |
|---|---|---|---|
| 5,184,625 A | 2/1993 | Cottone, Jr. et al. | |
| 5,492,119 A | 2/1996 | Abrams | |
| 5,624,736 A | 7/1997 | Avitall | |
| 5,642,736 A | 7/1997 | Avitall | |
| 5,836,960 A | 11/1998 | Kolesa et al. | |
| 5,916,214 A | 6/1999 | Cosio et al. | |
| 6,152,144 A | 11/2000 | Lesh et al. | |
| 6,582,443 B2 | 6/2003 | Cabak et al. | |
| 6,716,238 B2 | 4/2004 | Elliott | |
| 6,783,510 B1* | 8/2004 | Gibson | A61M 25/0147 604/528 |
| 6,941,169 B2 | 9/2005 | Pappu | |
| 7,149,587 B2 | 12/2006 | Wardle et al. | |
| 7,497,844 B2 | 3/2009 | Spear et al. | |
| 7,509,169 B2 | 3/2009 | Eigler et al. | |
| 7,566,336 B2 | 7/2009 | Corcoran et al. | |
| 7,623,899 B2 | 11/2009 | Worley et al. | |
| 7,647,124 B2 | 1/2010 | Williams | |
| 8,032,220 B2 | 10/2011 | Kuzma | |
| 8,473,023 B2 | 6/2013 | Worley et al. | |
| 8,500,733 B2 | 8/2013 | Watson | |
| 8,634,919 B1 | 1/2014 | Hou et al. | |
| 8,795,328 B2 | 8/2014 | Miles et al. | |
| 9,126,032 B2 | 9/2015 | Khairkhahan et al. | |
| 9,155,882 B2 | 10/2015 | Grubac et al. | |
| 9,220,906 B2 | 12/2015 | Griswold et al. | |
| 9,446,248 B2 | 9/2016 | Sheldon et al. | |
| 9,468,773 B1 | 10/2016 | Anderson et al. | |
| 9,492,674 B2 | 11/2016 | Schmidt et al. | |
| 2002/0165537 A1 | 11/2002 | Kelley et al. | |
| 2002/0183824 A1 | 12/2002 | Borgersen et al. | |
| 2004/0133089 A1 | 7/2004 | Kilcoyne et al. | |
| 2004/0147973 A1 | 7/2004 | Hauser | |
| 2004/0215307 A1 | 10/2004 | Michels et al. | |
| 2005/0004602 A1 | 1/2005 | Hart et al. | |
| 2005/0004641 A1 | 1/2005 | Pappu | |
| 2005/0136385 A1 | 6/2005 | Mann et al. | |
| 2006/0247753 A1 | 11/2006 | Wenger et al. | |
| 2007/0083230 A1 | 4/2007 | Javois | |
| 2007/0156114 A1 | 7/2007 | Worley et al. | |
| 2008/0057100 A1 | 3/2008 | Williams et al. | |
| 2008/0319424 A1* | 12/2008 | Muni | A61B 5/411 604/890.1 |
| 2009/0171159 A1* | 7/2009 | Jorgensen | A61B 1/05 600/139 |
| 2009/0287187 A1* | 11/2009 | Legaspi | A61M 25/0054 604/523 |
| 2010/0094314 A1 | 4/2010 | Hernlund et al. | |
| 2010/0274227 A1 | 10/2010 | Khairkhahan et al. | |
| 2011/0144572 A1 | 6/2011 | Kassab et al. | |
| 2011/0251660 A1 | 10/2011 | Griswold | |
| 2012/0059448 A1 | 3/2012 | Parker et al. | |
| 2012/0172690 A1 | 7/2012 | Anderson et al. | |
| 2012/0172892 A1 | 7/2012 | Grubac et al. | |
| 2012/0190927 A1* | 7/2012 | Uihlein | A61B 1/0053 600/149 |
| 2012/0197373 A1 | 8/2012 | Khairkhahan et al. | |
| 2013/0079798 A1* | 3/2013 | Tran | A61N 1/37205 606/129 |
| 2013/0103047 A1* | 4/2013 | Steingisser | A61N 1/3756 606/129 |
| 2013/0131591 A1 | 5/2013 | Berthiaume et al. | |
| 2013/0131693 A1 | 5/2013 | Berthiaume et al. | |
| 2013/0253342 A1 | 9/2013 | Griswold et al. | |
| 2013/0253347 A1 | 9/2013 | Griswold et al. | |
| 2014/0088656 A1 | 3/2014 | Cabelka et al. | |
| 2014/0330325 A1 | 11/2014 | Thompson-Nauman et al. | |
| 2014/0330326 A1 | 11/2014 | Thompson-Nauman et al. | |
| 2014/0330329 A1 | 11/2014 | Thompson-Nauman et al. | |
| 2015/0039070 A1 | 2/2015 | Kuhn et al. | |
| 2015/0051612 A1 | 2/2015 | Schmidt et al. | |
| 2015/0094668 A1 | 4/2015 | Wood et al. | |
| 2015/0094735 A1 | 4/2015 | Ward et al. | |
| 2015/0273207 A1 | 10/2015 | Tran et al. | |
| 2015/0306375 A1 | 10/2015 | Marshall et al. | |
| 2015/0306410 A1 | 10/2015 | Marshall et al. | |
| 2016/0015968 A1 | 1/2016 | Bonner et al. | |
| 2016/0067446 A1 | 3/2016 | Klenk et al. | |
| 2016/0067447 A1 | 3/2016 | Paspa et al. | |
| 2016/0220829 A1 | 8/2016 | Wood | |

FOREIGN PATENT DOCUMENTS

| | | |
|---|---|---|
| WO | 2004028348 A2 | 4/2004 |
| WO | WO 2013/043671 A1 | 3/2013 |
| WO | WO 2013/062793 A1 | 5/2013 |
| WO | 2015017157 A1 | 2/2015 |

OTHER PUBLICATIONS (PCT/US2015/040870) PCT Notification of Transmittal of the International Search Report and the Written Opinion of the International Searching Authority, dated Oct. 14, 2015, 10 pages.

(PCT/US2015/043957) PCT Notification of Transmittal of the International Search Report and the Written Opinion of the International Searching Authority, dated Nov. 11, 2015, 9 pages.

(PCT/US2014/057727) PCT Notification of Transmittal of the International Search Report and the Written Opinion of the International Searching Authority.

(PCT/US2014/057596) PCT Notification of Transmittal of the International Search Report and the Written Opinion of the International Searching Authority.

* cited by examiner

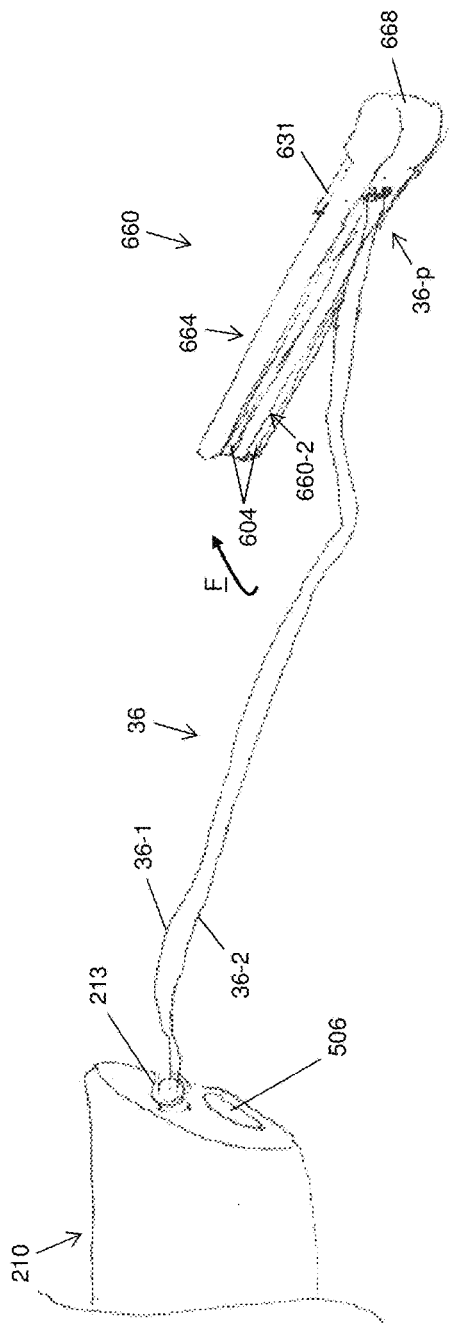
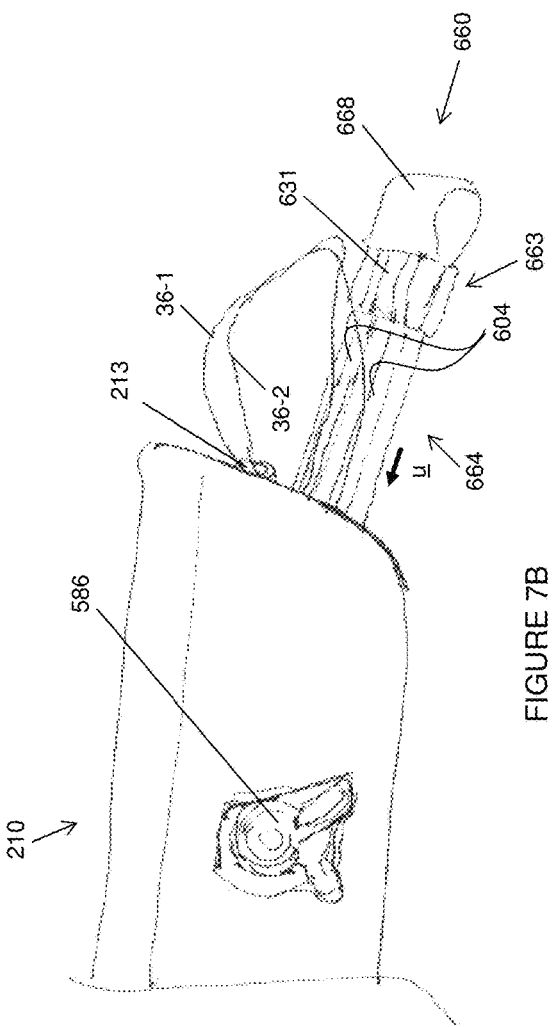
FIGURE 7A
FIGURE 7B

TOOLS AND ASSEMBLIES THEREOF FOR IMPLANTABLE MEDICAL DEVICES

CROSS-REFERENCE TO RELATED APPLICATION

The present application is related to commonly assigned U.S. patent application Ser. No. 14/039,937, now U.S. Pat. No. 9,526,522, entitled INTERVENTIONAL MEDICAL SYSTEMS, TOOLS, AND ASSEMBLIES, and which is incorporated by reference in its entirety.

FIELD OF THE DISCLOSURE

The present invention pertains to implantable medical devices, and more particularly to tools and related assemblies that are configured to facilitate percutaneous transvenous deployment of relatively compact implantable medical devices.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of implantable cardiac pacing devices that are wholly contained within a relatively compact package for implant in close proximity to the pacing site, for example, within the right ventricle RV of the heart. With reference to FIG. 1, such an implantable medical device 100 is illustrated, wherein an hermetically sealed housing 105, preferably formed from a biocompatible and biostable metal such as titanium, contains a pulse generator, or an electronic controller (not shown), to which at least one electrode 111 is coupled, for example, by a hermetic feedthrough assembly (not shown) like those known to those skilled in the art of implantable medical devices. Housing 105 may be overlaid with an insulative layer, for example, medical grade polyurethane, silicone, or parylene.

FIG. 1 further illustrates a distal portion of a standard guiding catheter 150 having been maneuvered up through the inferior vena cava IVC and into the right ventricle RV from the right atrium RA, according to methods known in the art of interventional cardiology. Although catheter 150 may be employed to deliver device 100 to the right ventricle RV, for implant, more sophisticated tools, which are more suitable to facilitate deployment of relatively compact implantable devices, like device 100, are desired.

SUMMARY

According to some embodiments of the present invention, a tool that facilitates deployment of an implantable medical device has an elongate inner assembly, which includes a single pull wire and a distal member configured to engage the medical device, and an elongate outer assembly, which includes a deployment tube; wherein the deployment tube extends around, and is moveable with respect to the inner assembly, and includes an enlarged distal-most portion, to contain the engaged device, prior to deployment. The deployment tube further includes an articulating segment, which is located just proximal to the enlarged distal-most portion, and which is defined by a composite sidewall. The composite sidewall includes a relatively soft section and a relatively stiff section that extend alongside one another, and along a length of the articulating segment, such that, when the single pull wire of the inner assembly is actuated, for example, by a control member included in a handle assembly of the tool, the composite sidewall causes the articulating segment of the deployment tube to bend in two directions. Such bending may be useful to direct the enlarged distal-most portion of the deployment tube toward a target implant site, for example, along a septum of the right ventricle RV. According to some preferred embodiments, the deployment tube further includes a segment having a preformed curvature that is located just proximal to the articulating segment, wherein the relatively stiff and soft sections of the composite wall of the articulating segment may meet, or abut one another along a line that is tangent to an outside of the pre-formed curve, and along a similar line that is on an opposite side of the deployment tube.

The tool, according to some embodiments, has a handle assembly that includes the aforementioned control member for the pull wire, another control member to move the deployment tube of the outer assembly, and further includes a proximal port and a flushing subassembly. The proximal port is in fluid communication with at least one lumen of the inner assembly, for example, to allow passage of an elongate tether therethrough, wherein the tether extends through the at least one lumen and has a distal end secured to the engaged device; and the flushing assembly includes a flush lumen, which is also in fluid communication with the at least one lumen of the inner assembly, and a connector port, which is coupled to flush lumen, wherein the connector port is located at an end of the handle assembly that is opposite the proximal port. According to some preferred embodiments, the proximal port and the flush lumen are also in fluid communication with an interior of the deployment tube, along a length of the inner assembly, for example, via one or more ports formed in the inner assembly.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and:

FIG. 7A is a perspective view of the tether assembly in relation to the handle assembly of the tool, according to some embodiments; and FIG. 7B is another perspective view of the tether assembly in relation to the handle assembly, according to some embodiments.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 2A:
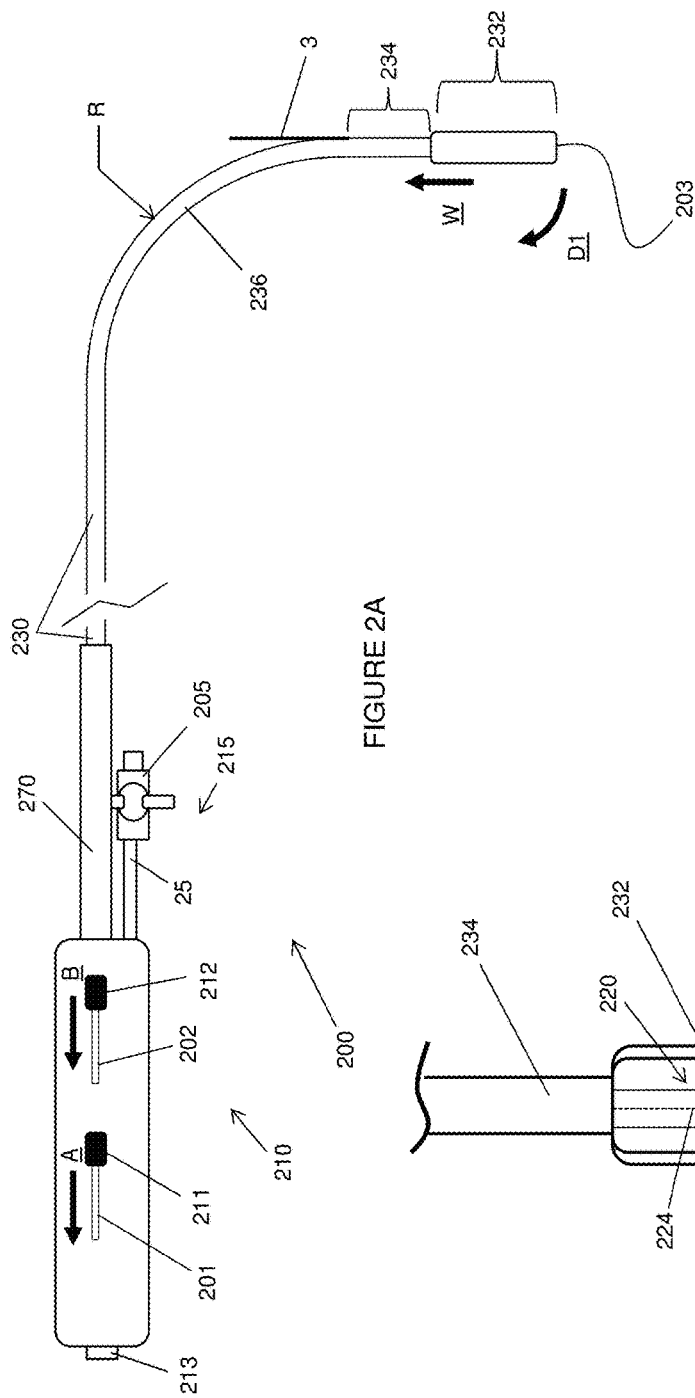
FIG. 2A is a side view of a tool that may be included in an interventional medical system, according to some embodiments.
Figure 2B:
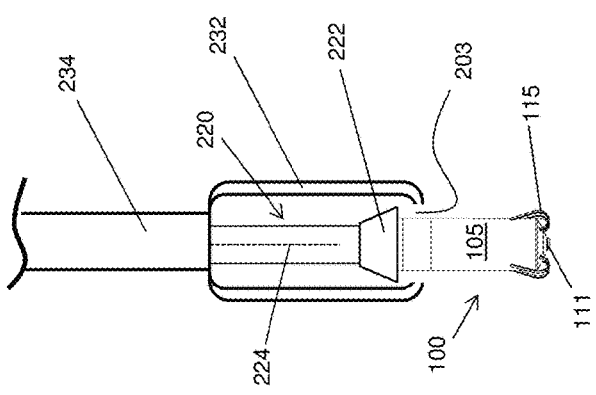
FIG. 2B is an enlarged view of a distal end of the tool, with a partial cut-away section view, according to some embodiments.

FIG. 2A is a side view of a tool 200 that may be included in an interventional medical system, according to some embodiments. FIG. 2A illustrates tool 200 including a handle assembly 210, and an outer assembly, which is formed by an elongate deployment tube 230 and an outer, stabilizing sheath 270 that surrounds a proximal portion of deployment tube 230, in proximity to handle assembly 210. FIG. 2A further illustrates deployment tube 230 including an enlarged distal-most portion 232, which is sized to contain an implantable medical device, for example, the above-described device 100; enlarged distal-most portion 232 also defines a distal opening 203 of deployment tube 230, for example, as seen in the cut-away section view of FIG. 2B. FIG. 2B illustrates tool 200 further including an elongate inner assembly 220, around which deployment tube 230 extends, wherein inner assembly 220 includes a distal member 222, which is configured to engage device, for example, by abutting an end of device 100, and a single pull wire 224, which is anchored adjacent to member 222. Pull wire 224 preferably extends within a lumen of inner assembly 220, for example, as described below, in conjunction with FIG. 3B. With reference back to FIG. 2A, a first control member 211 of handle assembly 210 is coupled to pull wire 224, and a second control member 212 is coupled to deployment tube 230.

Figure 1:
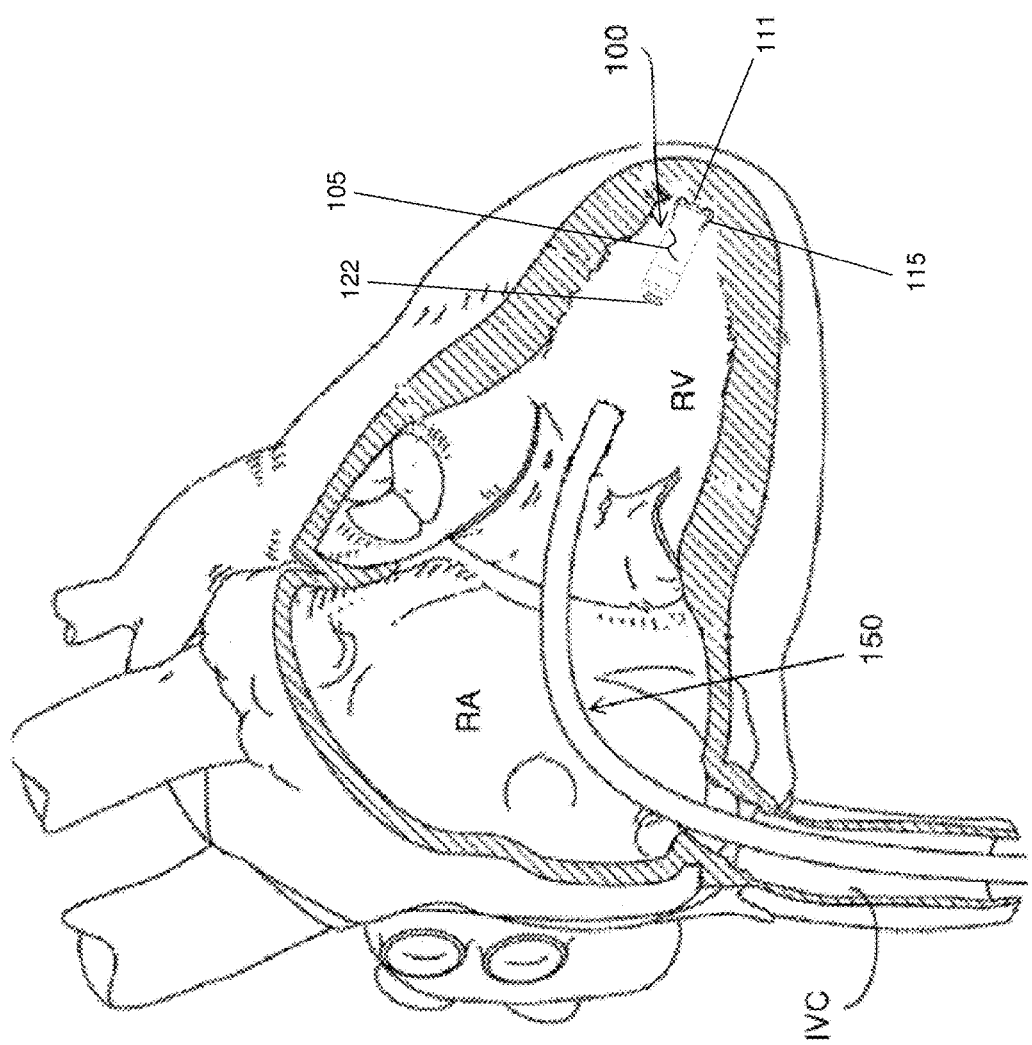
FIG. 1 is a schematic showing an example of an implanted medical device for cardiac stimulation.

According to the illustrated embodiment, movement of first control member 211, per arrow A, actuates pull wire 224 to bend inner assembly 220 and deployment tube 230 (described in greater detail below), and movement of second control member 212, per arrow B, moves deployment tube 230, per arrow W, to withdraw, or retract tube 230 relative to stabilizing sheath 270, inner assembly 220, and device 100, for example, from a first position, in which device 100 and distal member 222 of inner assembly 220 are contained within distal-most portion 232 of tube 230 (FIG. 2A), to a second position, at which device has passed out through distal opening 203 (FIG. 2B). The end of device 100 that is engaged by member 222 may include a tether attachment structure, for example, like a structure 122 illustrated in FIGS. 1 and 6, according to some embodiments in which the interventional medical system that includes tool 200 further includes an elongate tether that extends within one or a pair of lumens of inner assembly 220 and out through a proximal port 213 (FIG. 2A) of handle assembly 210. An exemplary tether will be described in further detail below. FIGS. 1 and 2B further illustrate implantable medical device 100 including a fixation member 115, which is mounted to an opposite end of device housing 105, in proximity to the aforementioned electrode 111, such that upon actuation of pull wire 224 and subsequent retraction of deployment tube 230, fixation member 115 is directed and exposed to secure device 100 at a target implant site so that electrode 111 is held in intimate contact with the tissue at the site.

According to an exemplary embodiment, enlarged distal-most portion 232 has an inner diameter of approximately 0.275 inch (~0.7 cm) and an outer diameter of approximately 0.3 inch (~0.8 cm). Although FIGS. 2A-B illustrate the outer diameter of distal-most portion 232 being enlarged from a remainder of deployment tube 230, for example, over a length of approximately 3.5 cm (~1.4 inch), according to alternate embodiments, an outer diameter along a more significant length, up to an entire length of deployment tube 230, may be the same as that of distal-most portion 232. A length of deployment tube 230, between handle assembly 210 and distal opening 203 of deployment tube 230, when tube 230 is in the first position (FIG. 2A), may be between approximately 103 cm and approximately 107 cm, for example, to reach the right ventricle RV from a femoral access site, for example, as described below, in conjunction with FIG. 4C.

Figure 3B:
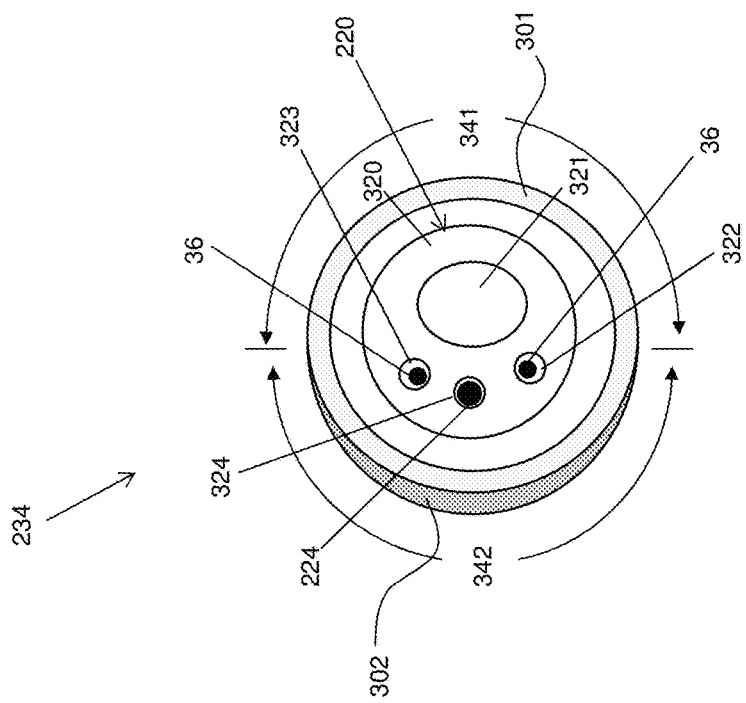
FIG. 3B is a cross-section view through section line B-B of FIG. 3A, according to some embodiments.
Figure 3A:
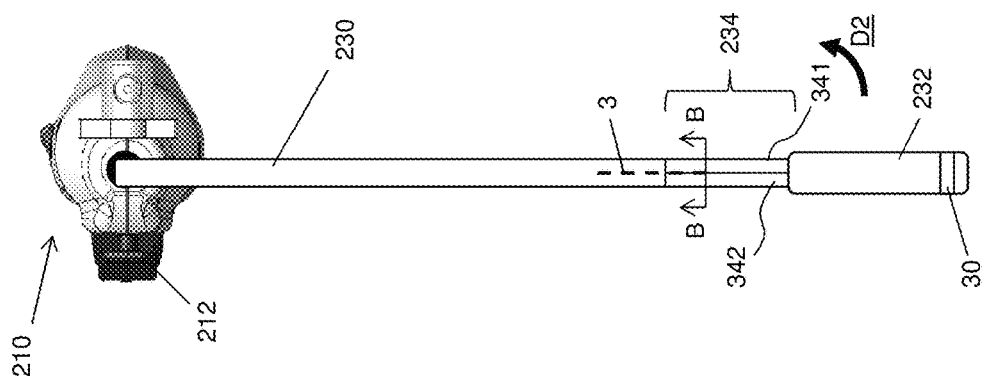
FIG. 3A is an end view of the tool, according to some embodiments.

FIG. 2A further illustrates deployment tube 230 including an articulating segment 234 located just proximal to enlarged distal-most portion 232. Articulating segment 234 may extend over a length of up to approximately 10 cm, preferably approximately 5.8 cm, and is defined by a composite sidewall that is constructed to bend in two directions in response to the aforementioned actuation of pull wire 224. FIG. 3A is an end view of tool 200; and FIG. 3B is a cross-section view through section line B-B of FIG. 3A, according to some embodiments, by which an exemplary construction of the composite sidewall is shown. FIG. 3A illustrates the composite sidewall including a relatively soft section 341 and a relatively stiff section 342, which extend alongside one another and along the length of articulating segment 234. FIG. 3B illustrates the composite sidewall of articulating segment 234 including a first, inner portion 301, which extends 360 degrees around inner assembly 220, and a second, outer portion 302, which extends approximately 180 degrees around inner layer 301, for example, being bonded thereto, such that inner portion 301, itself, forms relatively soft section 341, and the combination of inner portion 301 and outer portion 302 forms relatively stiff section 342. According to some embodiments, first portion 301 includes an inner layer, which lines an interior of deployment tube 230 and is surrounded, or reinforced by a metal braid, for example, a polyether block amide, such as PEBAX® 6333, with a stainless steel braid (e.g., 0.0018"× 0.008"×45 PPI), and an outer layer, which overlays the inner layer, for example, another grade of polyether block amide, such as PEBAX® 5533, wherein second portion 302 may be formed by a another grade of polyether block amide, for example PEBAX® 7233. According to the illustrated embodiment, when the single pull wire 224 is actuated, via control member 211, the composite sidewall causes articulating segment 234 to bend in a first direction, per arrow D1 (FIG. 2A), and in a second direction, per arrow D2 (FIG. 3A), toward relatively soft section 341, which is more flexible, or provides less resistance to bending than relatively stiff section 342.

Enlarged distal-most portion 232 is preferably formed separately from segment 234, for example, from another grade of polyether block amide, such as PEBAX® 7233, and then thermally bonded to segment 234. According to some preferred embodiments, distal-most portion 232 of deployment tube 230 is fitted with a radiopaque marker 30 (FIG. 3A), for example, a gold foil, with an adhesive backing, which is sandwiched between layers of the polyether block amide, in proximity to distal opening 203, and distal member 222 of inner assembly 220 is radiopaque, so that the retraction of tube 230, relative to member 222, can be observed via fluoroscopy. As was mentioned above, the outer diameter of distal-most portion 232 of deployment tube is shown enlarged from a remainder of deployment tube 230, (e.g., over a length of approximately 3.5 cm), which may be preferred, so that a majority of the length of deployment tube 230 has a smaller outer diameter, which allow for a smaller introducer sheath to provide access for tool 200 into a patient's venous system. Thus, the aforementioned exemplary construction of marker band 30, from a flexible gold foil, allows for some deformation of enlarged distal-most portion 232, when passing through the smaller introducer sheath, upon initial insertion of tool 200 into the patient's venous system.

With further reference to FIG. 2A, deployment tube 230 includes a segment 236 having a pre-formed curvature, which is located just proximal to articulating segment 234, wherein a length of segment 236 may be up to approximately 20 cm. According to the illustrated embodiment, the pre-formed curvature of segment 236 orients distal-most portion 232 of deployment tube 230 at an angle of approximately 90 degrees with respect to a length of tube 230 that extends proximally from segment 236 toward handle assembly 210. A radius R about which the pre-formed curvature extends may be between approximately 9 cm and approximately 13 cm. The curvature may be formed in deployment tube 230 prior to the assembly of inner assembly 220 therein, for example, by heat setting methods known in the art. With further reference to FIG. 3A, in conjunction with FIG. 2A, relatively soft section 341 and relatively stiff section 342 of the composite wall of articulating segment 234 meet, or abut one another along a line 3 (dashed, in FIG. 3A) that is tangent to an outside of the pre-formed curvature, and along a similar line on an opposite side of deployment tube 230.

Segment 236, and the length of deployment tube 230 that extends proximally therefrom, may be any suitable construction known in the art, to achieve a graduated flexibility and the necessary pushability and torque transfer that facilitates the maneuverability of tool 200 to a target implant site. For example, the aforementioned construction of inner portion 301 of articulating segment 234 may extend proximally along segment 236 and the proximal length to handle assembly 210, wherein varying durometers of polyether block amide are used for the outer layer, to transition the stiffness/flexibility along the length of deployment tube 230.

FIG. 3B further illustrates inner assembly 220 including a multi-lumen tube 320 to which distal member 222 is coupled (FIG. 2B), according to some embodiments. Multi-lumen tube 320 may be extruded polyether block amide, polyurethane, or silicone rubber, or a composite thereof, and may include an overlay (not shown), for example, formed of braid-reinforced polyether block amide. According to the illustrated embodiment, multi-lumen tube 320 includes one, relatively large lumen 321, and three, relatively small lumens 322-324, wherein pull wire 224 extends within lumen 324, and lumens 321-323 are in fluid communication with distal opening 203 of deployment tube 230, and with proximal port 213 of handle assembly 210 (FIGS. 2A-B). According to an exemplary embodiment, pull wire 224 has a diameter of approximately 0.009 inch (~0.23 mm) and is formed from medical grade 304 stainless steel, which is preferably coated with a fluoropolymer such as polytetrafluoroethylene (PTFE). It should be noted that the orientation, relative to sections 341, 342 of articulating segment 234, of pull wire 224, within lumen 324 is not necessarily fixed, so may vary from that illustrated in FIG. 3B.

Lumens 322, 323 of multi-lumen tube 320 are preferably sized to accommodate first and second lengths of an elongate tether 36, for example, being looped and secured to tether attachment structure 122 of device 100, when the end of device 100 abuts distal member 222 of inner assembly 220, as shown in FIG. 2B. Elongate tether 36 may be part of a tether assembly 600, according to some embodiments of the interventional medical system, which will be described below, in conjunction with FIGS. 6-7B. Although the inclusion of separate lumens 322, 323, to accommodate the first and second lengths of the looped tether, are useful in preventing a tangling of the first and second lengths, according to some alternate embodiments, multi-lumen tube 320 need not include lumens 322, 323, and both lengths of the looped tether 36 may extend in lumen 321. In either case, it should be noted that proximal port 213 of handle assembly 210 accommodates passage of tether 36 therethrough, to provide an operator of tool 200 access to tether 36. Lumen 321 of multi-lumen tube 320 is preferably sized to accommodate a snare (not shown), which may be inserted therein, through proximal port 213, and used to retrieve device 100, if necessary, from an implant site, after tether 36 is cut and disengaged from tether attachment structure 122 of device 100.

With reference back to FIG. 2A, handle assembly 210 further includes a flushing subassembly 215. FIG. 2A illustrates flushing subassembly 215 including a connector port 205, for example, to which a saline-filled syringe may be attached, and a flexible tube 25 that defines a flush lumen in fluid communication with lumens 321-323 of multi-lumen tube 320. Flushing of tool 200, via subassembly 215, is useful to purge air therefrom, and is further described below, in conjunction with FIGS. 5A-B.

Figure 4B:
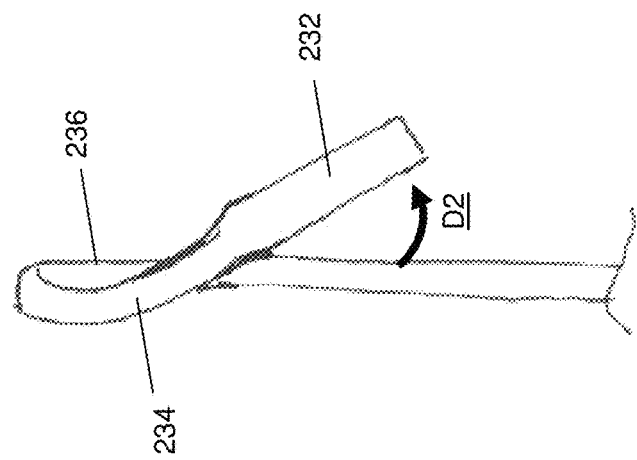
FIGS. 4A-B are a side view and a corresponding bottom view of the tool, upon actuation of a single pull wire thereof, according to some embodiments.
Figure 4A:
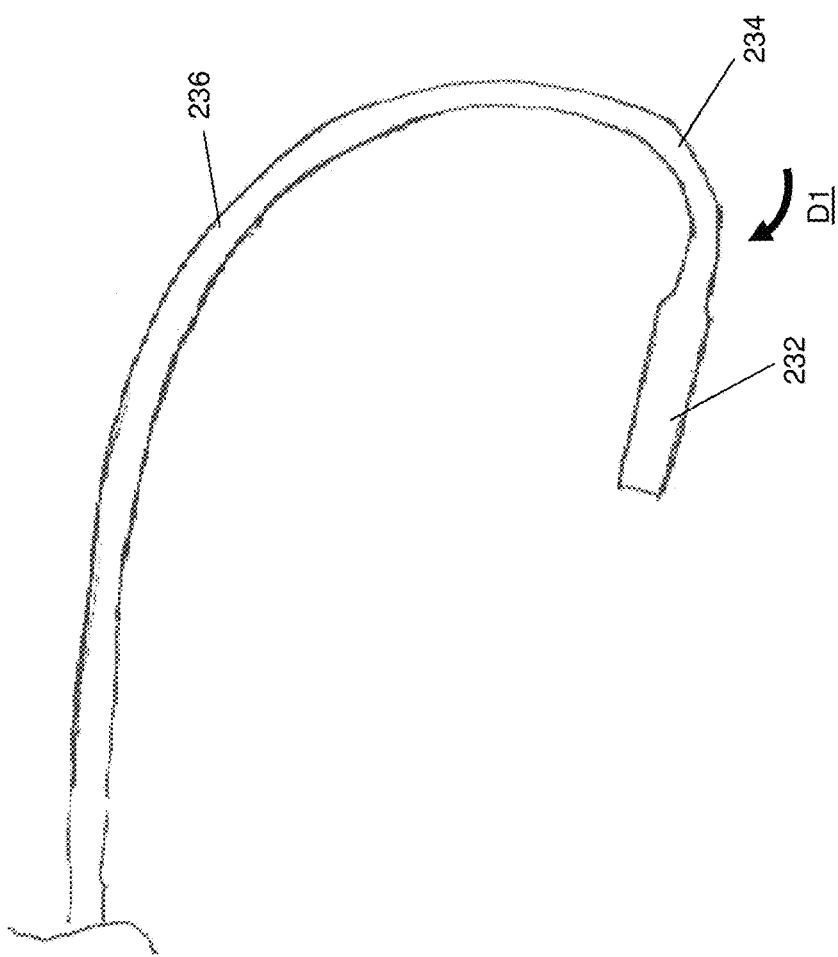
Figure 4C:
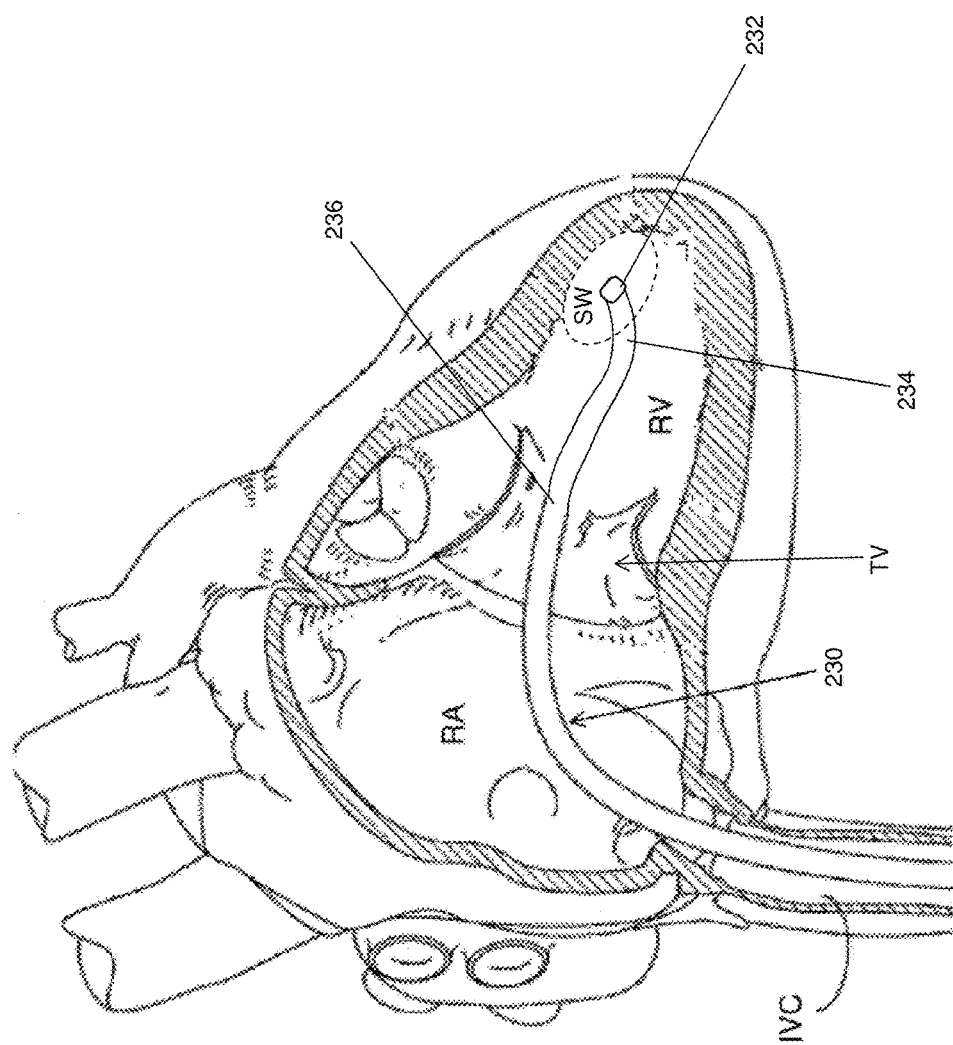
FIG. 4C is a schematic showing the tool within a right ventricle of a heart.

Turning now to FIGS. 4A-C, the significance of the response of articulating segment 234 of deployment tube 230, to the actuation of the single pull wire 224 will be described. FIGS. 4A-B are a side view and a corresponding bottom view of tool 200, respectively, upon actuation of pull wire 224; and FIG. 4C is a schematic showing tool 200 within the right ventricle RV of a heart, for example, having been introduced into a patient's venous system through an introducer sheath at a femoral access site. FIGS. 4A-B illustrate the aforementioned bending of articulating segment 234 in the first and second directions D1, D2, respectively, in response to actuation of the single pull wire 224 via control member 211 (FIG. 2A). It should be noted that that the pre-formed curvature of segment 236 can facilitate the navigation of tool 200 within the heart, for example, once distal-most portion 232 has been passed into the RA of the heart, via the IVC, by orienting distal-most portion 232 of deployment tube 230 for passage through the tricuspid valve TV and into the right ventricle RV. Then, with reference to FIG. 4C, once distal-most portion 232 has been passed into the right ventricle RV, actuation of the single pull wire 224, for example, via control member 211 (FIG. 2A), results in the simultaneous bending of articulating segment 234, in first direction D1 (FIG. 4A) and second direction D2 (FIG.

4B), to direct enlarged distal-most portion 232 of deployment tube 230 toward a target site that is located along a septal wall SW in an apical region of the right ventricle RV. Then, device 100 may be deployed through distal opening 203 of deployment tube 230, by the retraction thereof relative to inner assembly 220, for example, via control member 212 (FIG. 2A), as was described above. Thus, the composite sidewall construction of articulating segment 234 allows for a simplified construction of tool 200 that includes only the single pull wire 224 and corresponding control member 211 for articulation; furthermore, such a construction can make tool 200 easier to use.

Figure 5A:
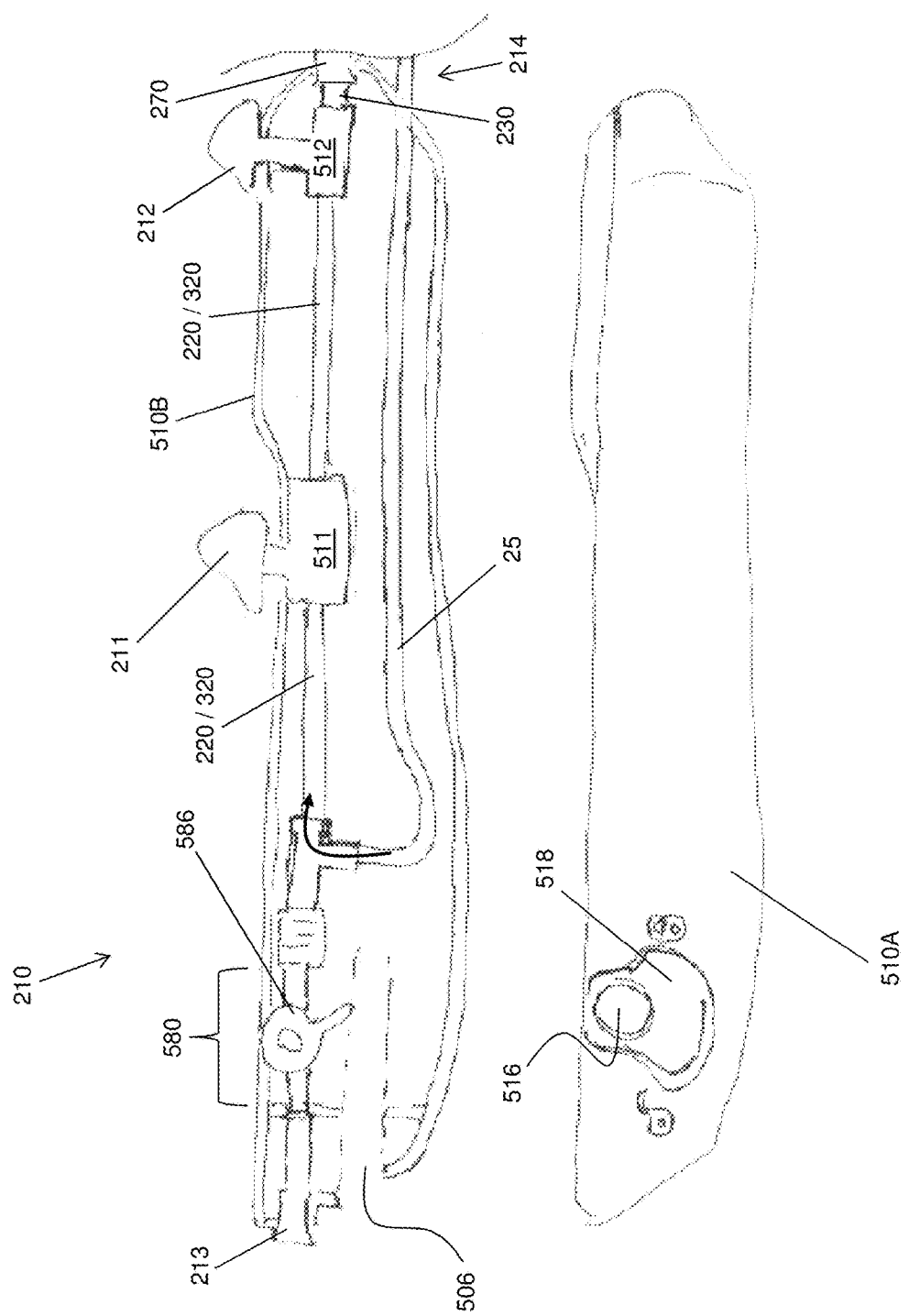
FIG. 5A is a plan view of a handle assembly of the tool, according to some embodiments.

FIG. 5A is a plan view of handle assembly 210 of tool 200, according to some embodiments, wherein a first portion of an outer surface, or shell 510A of handle assembly 210 is removed to see an arrangement of components within a second portion of the shell 510B. FIG. 5A illustrates first control member 211 including a base portion 511 that wraps around a portion of multi-lumen tube 320 of the above-described inner assembly 220, which extends into handle assembly 210, so that a first end of the aforementioned pull wire 224, for example, that extends out from lumen 324 (FIG. 3B) through an opening (not shown) in the sidewall of tube 320, may be coupled to first control member 211, for example, by engaging the first end within base portion 511. With reference back to FIG. 2A, control member 211 is movable within a slot 201, which extends through shell 510A, 510B, relative to inner assembly 220/multi-lumen tube 320, which is fixed in handle assembly 210 by connection to a tether engaging conduit 580 and the aforementioned flexible tube 25 of flushing subassembly 215, which is shown routed within handle assembly 210. FIG. 5A further illustrates second control member 212 including a base portion 512, which is coupled to a proximal end of deployment tube 230 within handle assembly 210, and, like first control member 211, second control member 212 is moveable in a corresponding slot 202, which may be seen in FIG. 2A, to move deployment tube 230 between the above-described first and second positions. According to some embodiments, a seal member (e.g., a silicone O-ring; not shown), which may be lubricated, for example, with silicone oil, forms a dynamic sealing interface between deployment tube 230 and inner assembly 220 in proximity to first control member 211.

The aforementioned stabilizing sheath 270 is also shown extending within handle assembly 210, for example, being coupled thereto in proximity to a distal end 214 of handle assembly 210. With further reference to FIG. 2A, sheath 270 extends along a limited proximal length of the outer assembly and may be relatively rigid to facilitate the movement of deployment tube 230, for example, by preventing an operator who is handling tool 200 from inadvertently applying a force around tube 230 in proximity to handle assembly 210, which force could impede the movement of tube 230 relative to handle assembly 210 and inner assembly 220. Sheath 270 may also provide an enhanced interface between tool 200 and a valve of an introducer sheath, for example, an interface that provides improved sealing and/or additional radial strength to counteract a compressive force of the valve, which, if the valve is a Tuohy Borst type, can be tightened down around tool 200 to different degrees depending upon the operator.

Figure 6:
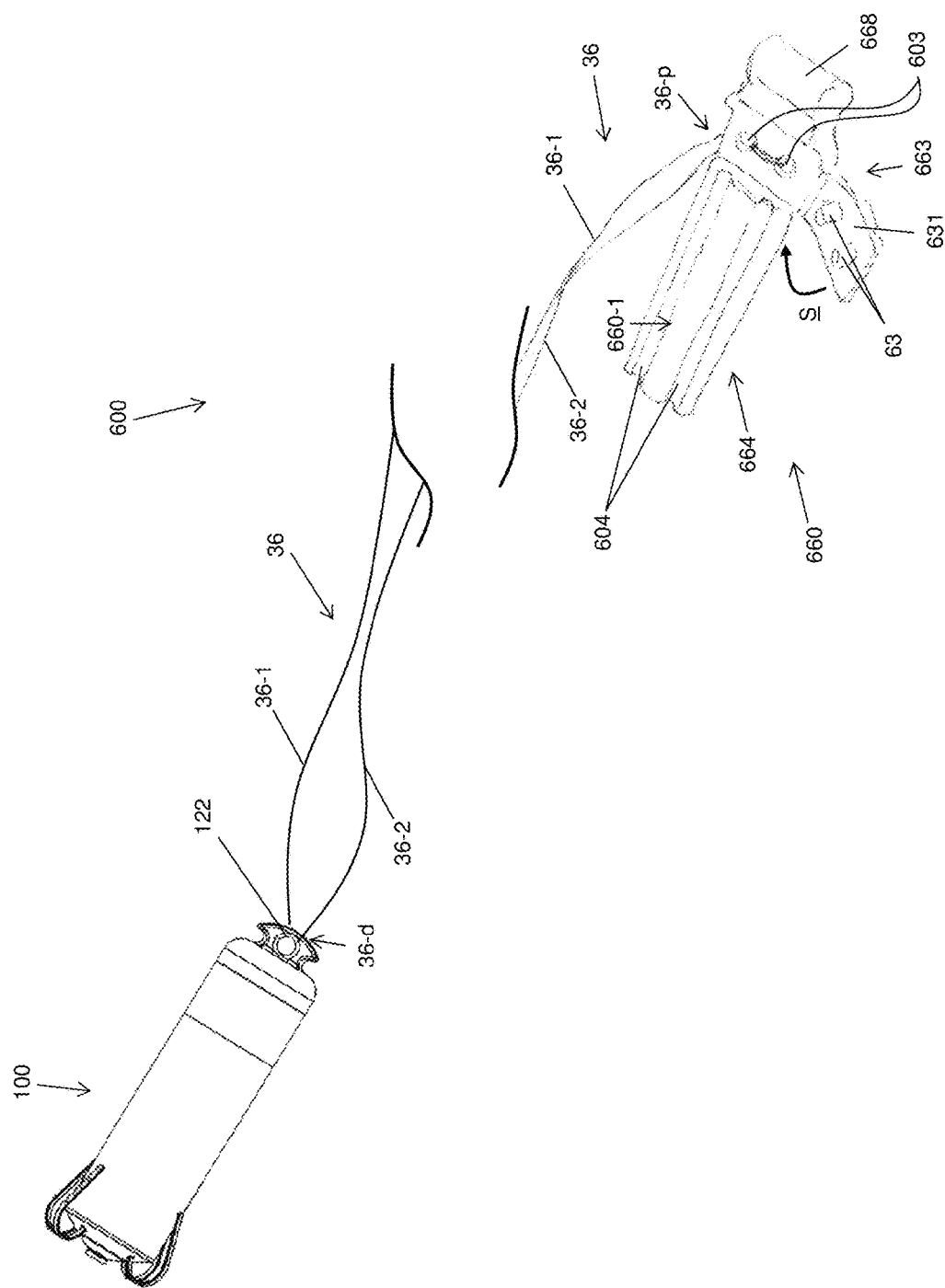
FIG. 6 is a perspective view of a tether assembly coupled to an implantable medical device, according to some embodiments.

With further reference to FIG. 5A, handle assembly 210 includes a receptacle 506 located in proximity to proximal port 213, wherein receptacle 506 is configured to receive a tether holder 660 of a tether assembly 600, which also includes the aforementioned elongate tether 36, and which is illustrated in FIG. 6. As was mentioned above, proximal port 213 allows tether 36 to pass therethrough, to exit tool 200, and FIG. 5A further illustrates tether engaging conduit 580 connecting inner assembly 220 to proximal port 213, thereby allowing passage of tether 36 from inner assembly 220 (e.g., lumens 322, 323 of multi-lumen tube 320) to proximal port 213. Conduit 580 may also allow passage of the aforementioned snare therethrough and into inner assembly 220 (e.g., lumen 321 of multi-lumen tube 320), for delivery of the snare out through distal opening 203 (FIGS. 2A-B) of tool 200. Conduit 580 is described in greater detail below.

FIG. 6 is a perspective view of tether assembly 600 coupled to implantable medical device 100, according to some embodiments. FIG. 6 illustrates a distal end 36-*d* of tether 36 secured to attachment structure 122 of device 100, a proximal end 36-*p* of tether 36 attached to tether holder 660, and tether 36 formed in a loop, such that a first length 36-1 of tether 36 extends alongside a second length 36-2 of tether 36. With reference back to FIG. 3B, first length 36-1 may extend within lumen 322, and second length 36-2, within lumen 323 of multi-lumen tube 320, when device 100 is contained in enlarged distal-most portion 232 of deployment tube 230. FIG. 6 further illustrates tether holder 660 including a locking portion 663, for securing proximal end 36-*p* of tether 36, for example, as seen in FIGS. 7A-B, and a pin portion 664, for which receptacle 506 of handle assembly 210 is configured. Tether 36 may be formed from a polyester fiber having a fluoropolymer coating, such as PTFE, or any other suitable material, and tether holder 660 may be formed from a plastic, such as polypropylene, for example, by injection molding.

Locking portion 663 is shown including a pair of apertures 603, each of which extends from a first side 660-1 to a second side 660-2 (FIG. 7A) of tether holder 660, and a corresponding pair of plug members 63, wherein each plug member 63 is configured to fit within the corresponding aperture 603, alongside a corresponding length of proximal end 36-*p* of tether 36, in order to secure proximal end 36-*p* to tether holder 660; and pin portion 664 is shown including a pair of grooves 604, each groove 604 approximately aligned with a corresponding aperture 603 and configured to receive a corresponding length 36-1, 36-2 of tether 36 in proximity to proximal end 36-*p*. According to the illustrated embodiment, plug members 63 extend from a hinged flap 631 of locking portion 663, wherein flap 631 may be closed, per arrow S, to force plug members 63 into apertures 603, and then opened, to remove plug members 63 from apertures 603, when the operator desires to release of tether 36 from holder 660.

With reference to FIGS. 7A-B, which are perspective views of tether assembly 600 in relation to handle assembly 210, it may be appreciated that grooves 604 facilitate a folding of lengths 36-1, 36-2, for example, per arrow F (FIG. 7A), in proximity to the secured proximal end 36-*p*, around tether holder 660, without tangling, when pin portion 664 is inserted into receptacle 506. It may be seen in FIGS. 6 and 7A, that, according to some preferred embodiments, grooves 604 extend along first and second sides 660-1, 660-2 of tether holder 660. It should be noted that, according to some alternate embodiments, locking portion 663 of tether holder 660 may only include one aperture 603 and corresponding plug member 63, and, likewise, pin portion 664 may include a single groove 604 approximately aligned with the single aperture 603.

FIG. 7A illustrates lengths 36-1, 36-2 of tether 36 extending out from proximal port 213 of handle assembly 210, and proximal end 36-p of tether 36 being secured to tether holder 660 prior to folding lengths 36-1, 36-2 around holder 660, per arrow F. It should be understood that distal end 36-d of tether 36 is preferably secured to device 100 (FIG. 6), then threaded through inner assembly 220 (e.g., lumens 322, 323 of multi-lumen tube 320) just prior to loading device 100 into enlarged distal-most portion 232 of deployment tube 230, through distal opening 203 (FIGS. 2A-B), and then proximal end 36-p, which extends out from proximal port 213, is secured to tether holder 660, for example, as was described above. FIG. 7B illustrates pin portion 664 of tether holder 660, after tether 36 has been secured and folded thereabout, being inserted, per arrow u, into receptacle 506 of handle assembly 210, so that, as the operator uses handle assembly 210 to navigate and articulate of tool 200, as described above in conjunction with FIG. 4C, and to subsequently deploy device 100, tether 36 is neatly kept out of the way of the operator. FIGS. 6 and 7A-B further illustrate tether holder 660 including a knob 668, which can facilitate the handling of tether holder 660, for example, while securing tether 36 thereto, while folding tether 36 thereabout, for inserting tether holder 660 into receptacle 506, and for removing tether holder 660 from receptacle 506.

With further reference to FIG. 7B, in conjunction with FIG. 5A, tether engaging conduit 580 includes a valve member 586 integrated therein. According to an exemplary embodiment, valve member 586 is constructed like a stopcock valve known to those skilled in the art. FIG. 5A shows first portion of shell 510A of handle assembly 210 including an aperture 516, which is formed through a recessed surface 518 of portion 510A, and which provides access to valve member 586 so that an operator can move valve member 586 between an open position (FIG. 7A) and a closed position (FIG. 5A). In the open position, valve member 586 allows fluid communication between proximal port 213 of handle assembly 210 and lumens 321-323 (FIG. 3B) of inner assembly 220, and thus, free movement of tether 36 therethrough. When open, valve member 586 also allows passage of the aforementioned snare therethrough and into inner assembly 220, for example, lumen 321 of multi-lumen tube 320. In the closed position, valve member 586 clamps tether 36, and may provide hemostasis for tool 200, that is, prevent a back flow of bodily fluids through tool 200 during navigation and device deployment. Tether 36 is preferably clamped while the operator navigates and articulates tool 200, and deploys device 100, after which, the operator moves valve member 586 into the open position to release tether 36 therefrom; then, upon removing tether holder 660 from receptacle 506, the operator may grasp tether holder 660 and tug on device 100, via tether 36, to test the fixation thereof at the implant site. If device 100 is adequately fixed, and the implant site is satisfactory, the operator leaves valve member 586 in the open position so that, once proximal end 36-p is released from tether holder 660, one of lengths 36-1, 36-2 may be grasped to release tether 36 from device 100, and withdraw tether 36 out from inner assembly 220, through proximal port 213 of tool 200.

With further reference to FIG. 5A, in conjunction with FIG. 2A, flexible tube 25 of flushing subassembly 215, which defines the flushing lumen thereof, is routed within handle assembly 210 and extends out distal end 214 thereof, alongside sheath 270, where an end of tube 25 is coupled to connector port 205 (FIG. 2A). According to the illustrated embodiment, the location of connector port 205 at distal end 214 of handle assembly 210, which is generally opposite from proximal port 213, by virtue of the routing of tube 25 out distal end 214, can help to facilitate tether management, via tether holder 660 and receptacle 506, and the overall handling of tool 200, via handle assembly 210. As was mentioned above, the flush lumen defined by tube 25 is connected to inner assembly 220, and the arrow in FIG. 5A indicates the flow of a flushing fluid from the flush lumen to lumens of inner assembly 220 (e.g., lumens 321-323 of multi-lumen tube 320, FIG. 3B). FIG. 5A further illustrates the flush lumen being connected to tether engaging conduit 580, and, when valve member 586 of conduit 580 is in the closed position, flow of the flushing fluid, from flush lumen, is blocked from flowing out proximal port 213. It should be noted that, according to the illustrated embodiment, the lumens of inner assembly 220 may also be flushed via proximal port 213, when valve member 586 of conduit 580 is in the open position to allow the fluid communication between proximal port 213 and the lumens.

Figure 5B:
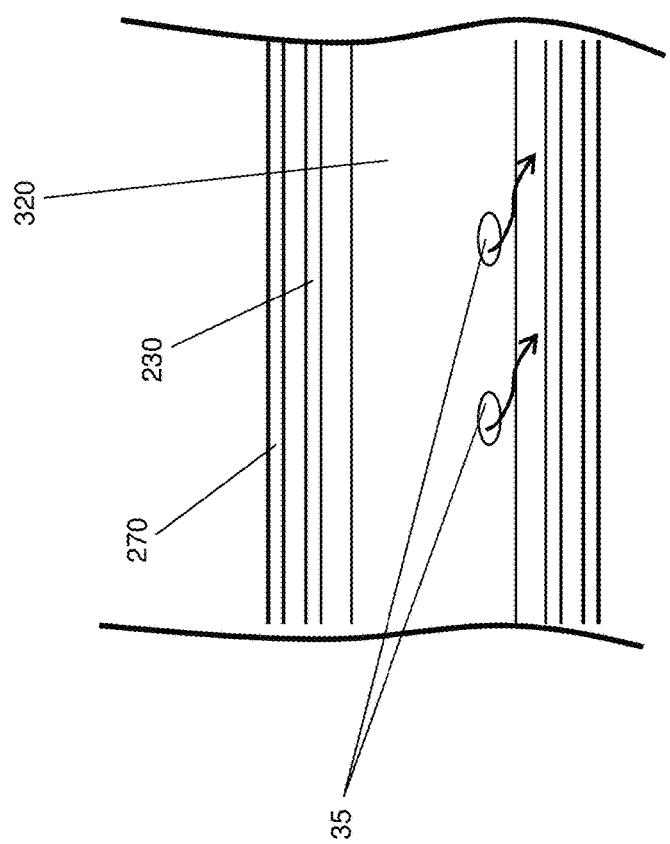
FIG. 5B is a cut-away section showing a portion of an inner assembly of the tool extending within an outer assembly of the tool, according to some embodiments.

According to some preferred embodiments, the flush lumen of flushing subassembly 215 is also in fluid communication with the interior of deployment tube 230, for example, an annular space formed between deployment tube 230 and inner assembly 220, along a length of inner assembly 220, for example, via one or more ports formed through a sidewall of multi-lumen tube 320. FIG. 5B is a cut-away section showing a portion of inner assembly 220 extending within the outer assembly of tool 200, just distal to handle assembly 210, according to some embodiments. FIG. 5B illustrates ports 35 formed through the sidewall of tube 320, for example, at lumen 321 (FIG. 3B), so that lumen 321 is in fluid communication with the interior of deployment tube 230, as indicated by the arrows, to allow flushing between the inner and outer assemblies of tool 200. Thus, tool 200 may be completely purged of air via flushing subassembly 215.

In the foregoing detailed description, the invention has been described with reference to specific embodiments. However, it may be appreciated that various modifications and changes can be made without departing from the scope of the invention as set forth in the appended claims.

The invention claimed is:

1. A tool facilitating deployment of an implantable medical device, the tool comprising:
 a handle assembly including a first control member and a second control member;
 an elongate inner assembly comprising a distal member and a single pull wire and defining a single lumen for the single pull wire, the single pull wire extending from the first control member of the handle assembly to an end of the single pull wire anchored adjacent to the distal member, and the distal member being configured to abut an end of the implantable medical device; and
 an outer assembly comprising an elongate deployment tube extending around the inner assembly and being longitudinally moveable by means of the second control member of the handle assembly relative to the inner assembly between first and second positions, the deployment tube including an enlarged distal-most portion and an articulating segment, and a preformed curvature, the articulating segment being located proximal to the enlarged distal-most portion, the preformed curvature being located proximal to the articulating segment of the deployment tube, the distal member of the inner assembly being located within the enlarged distal-most portion, and the enlarged distal-most portion defining a distal opening of the deployment tube;
 wherein the articulating segment of the deployment tube of the outer assembly is defined by a composite sidewall, the composite sidewall including a relatively soft section and a relatively stiff section, the sections extending alongside one another and along a length of the articulating segment and meeting along a line that is tangent to an outside of the preformed curvature such that when the single pull wire of the inner assembly is actuated in a single direction via the first control member the composite sidewall causes the articulating segment of the deployment tube to bend in a first direction and a second direction that is different than the first direction such that the articulating segment articulates in at least two geometric planes;

wherein the composite sidewall that defines the articulating segment of the deployment tube of the outer assembly comprises a first inner portion extending 360 degrees around the inner assembly to form the relatively soft section of the composite sidewall and a second outer portion extending approximately 180 degrees around the first inner portion to form the relatively stiff section of the composite sidewall;

wherein substantially an entirety of the implantable medical device is contained within the enlarged distal-most portion of the deployment tube when the deployment tube is in the first position and the end of the implantable medical device abuts the distal member; and wherein the implantable medical device passes out through the distal opening of the deployment tube when the deployment tube is in the second position.

2. The tool of claim 1, wherein the preformed curvature extends about a radius of between approximately 9 centimeters (cm) and approximately 13 cm, and the enlarged distal-most portion of the deployment tube is oriented by the curvature at an angle of approximately 90 degrees with respect to a length of the deployment tube that extends proximally from the preformed curvature.

3. The tool of claim 1, wherein the length of the articulating segment of the deployment tube of the outer assembly is between approximately 5 centimeters (cm) and approximately 7 cm.

4. The tool of claim 1, wherein the enlarged distal-most portion of the deployment tube of the outer assembly comprises a metal foil radiopaque marker band sandwiched between layers of polyether block amide.

5. The tool of claim 1, wherein the outer assembly further comprises an outer stabilizing sheath surrounding the deployment tube, the stabilizing sheath having a proximal end secured to the handle assembly, and the deployment tube being longitudinally moveable relative to the stabilizing sheath.

6. The tool of claim 1, wherein:
the inner assembly further includes a multi-lumen tube to which the distal member is coupled, the multi-lumen tube including the single lumen in which the single pull wire extends and at least one other lumen in fluid communication with the distal opening of the deployment tube of the outer assembly, the at least one other lumen being configured to receive an elongate tether, the tether being secured to the end of the device; and
the handle assembly further includes a proximal port in fluid communication with the at least one other lumen, the proximal port allowing passage of the tether therethrough.

7. The tool of claim 6, wherein the handle assembly further includes a flushing subassembly, the flushing subassembly including a connector port and a flush lumen extending therefrom, the flush lumen being in fluid communication with the at least one other lumen of the multi-lumen tube.

8. The tool of claim 7, wherein the flush lumen is also in fluid communication with an interior of the deployment tube of the outer assembly that surrounds the multi-lumen tube.

9. The tool of claim 1, wherein:
the inner assembly further includes a multi-lumen tube to which the distal member is coupled, the multi-lumen tube including the single lumen in which the single pull wire extends and at least one other lumen in fluid communication with the distal opening of the deployment tube of the outer assembly;
the handle assembly further includes a flushing subassembly and a proximal port in fluid communication with the at least one other lumen; and
the flushing subassembly includes a connector port and a flush lumen extending therefrom, the flush lumen being in fluid communication with the at least one other lumen of the multi-lumen tube.

10. The tool of claim 9, wherein the multi-lumen tube further includes at least one port formed through a sidewall thereof to create fluid communication between the at least one other lumen and an interior of the deployment tube of the outer assembly that extends around the multi-lumen tube so that the flush lumen is also in fluid communication with the interior of the deployment tube.

11. The tool of claim 1, wherein the deployment tube is configured to retract relative to the implantable medical device in the enlarged distal-most portion when the deployment tube moves from the first position to the second position to cause the implantable medical device to pass out through the distal opening of the deployment tube.

12. A deployment tube for a tool that facilitates deployment of an implantable medical device, the deployment tube comprising:
a proximal end coupled to a control member of a handle assembly of the tool;
an enlarged distal-most portion defining a distal opening of the deployment tube and forming a container for the implantable medical device, the deployment tube being configured for assembly around an inner assembly of the tool that comprises a distal member and a single pull wire such that the distal member of the inner assembly fits together with the implantable medical device in the container;
a first segment having a preformed curvature; and
a second articulating segment that defines a single lumen for the single pull wire and extends between the first segment and the enlarged distal-most portion, the second articulating segment being defined by a composite sidewall, the composite sidewall including a relatively soft section and a relatively stiff section, the sections extending alongside one another and along a length of the second articulating segment and meeting along a line that is tangent to an outside of the preformed curvature such that when the deployment tube is assembled around the inner assembly of the tool and the single pull wire of the inner assembly of the tool is actuated in a single direction the composite sidewall causes the second articulating segment of the deployment tube to bend in two directions;
wherein the composite sidewall that defines the second articulating segment comprises a first inner portion extending 360 degrees around a longitudinal axis of the deployment tube to form the relatively soft section of the composite sidewall and a second outer portion extending approximately 180 degrees around the first inner portion to form the relatively stiff section of the composite sidewall.

13. The deployment tube of claim 12, wherein the preformed curvature of the first segment extends about a radius of between approximately 9 centimeters (cm) and approximately 13 cm, and the enlarged distal-most portion is oriented by the curvature at an angle of approximately 90 degrees with respect to a proximal length of the deployment tube that extends proximally from the first segment.

14. The deployment tube of claim 12, wherein the length of the second articulating segment is between approximately 5 centimeters (cm) and approximately 7 cm.

15. The deployment tube of claim 12, wherein the enlarged distal-most portion comprises a metal foil radiopaque marker band sandwiched between layers of polyether block amide.

\* \* \* \* \*